(12) United States Patent
Chew et al.

(10) Patent No.: US 7,120,479 B2
(45) Date of Patent: Oct. 10, 2006

(54) SWITCH-MODE OXIMETER LED DRIVE WITH A SINGLE INDUCTOR

(75) Inventors: Bradford B Chew, San Ramon, CA (US); Ethan Petersen, Castro Valley, CA (US); William Shea, Livermore, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 101 days.

(21) Appl. No.: 10/787,852

(22) Filed: Feb. 25, 2004

(65) Prior Publication Data

US 2005/0187447 A1    Aug. 25, 2005

(51) Int. Cl.
*A61B 5/00* (2006.01)
*H05B 37/00* (2006.01)
(52) U.S. Cl. .................. 600/323; 600/310; 315/186
(58) Field of Classification Search ............... 600/310, 600/323; 315/186, 313; 356/41
See application file for complete search history.

(56) References Cited

U.S. PATENT DOCUMENTS

| | | | |
|---|---|---|---|
| 4,742,294 A * | 5/1988 | Gallios | 324/117 R |
| 4,802,486 A | 2/1989 | Goodman et al. | |
| 4,911,167 A | 3/1990 | Corenman et al. | |
| 4,928,692 A | 5/1990 | Goodman et al. | |
| 4,934,372 A | 6/1990 | Corenman et al. | |
| 5,165,162 A | 11/1992 | Charles | |
| 5,227,676 A * | 7/1993 | Bahr et al. | 327/94 |
| 5,351,685 A | 10/1994 | Potratz | |
| 5,368,026 A | 11/1994 | Swedlow et al. | |
| 5,662,106 A | 9/1997 | Swedlow et al. | |
| 5,713,355 A | 2/1998 | Richardson et al. | |
| 5,746,697 A | 5/1998 | Swedlow et al. | |
| 5,803,910 A | 9/1998 | Potratz | |
| 5,921,921 A | 7/1999 | Potratz et al. | |
| 5,924,979 A | 7/1999 | Swedlow et al. | |
| 6,198,405 B1 | 3/2001 | Andersson et al. | |
| 6,226,539 B1 | 5/2001 | Potratz | |
| 6,411,045 B1 * | 6/2002 | Nerone | 315/291 |
| 6,665,551 B1 | 12/2003 | Suzuki | |
| 6,897,754 B1 * | 5/2005 | Jeong et al. | 336/83 |

FOREIGN PATENT DOCUMENTS

GB          2044550          10/1980

* cited by examiner

*Primary Examiner*—Eric F. Winakur
(74) *Attorney, Agent, or Firm*—Fletcher Yoder PC

(57) ABSTRACT

A light emitter drive circuit for an oximeter which utilizes a single inductor for driving multiple light emitters. The inductor is connected to a switching circuit to multiple energy storage circuits, such as capacitors. These are alternately charged up, using the same inductor. Subsequently, the capacitors are alternately discharged for their corresponding light emitters through the same inductor. Also, the magnetic susceptibility of the LED drive circuit is reduced by using magnetic flux canceling in the inductor. In one embodiment, a toroidal inductor is used with geometric symmetry and its magnetic flux. In another embodiment, a dual core closed bobbin shielded inductor is used.

4 Claims, 3 Drawing Sheets

SWITCH-MODE OXIMETER LED DRIVE WITH A SINGLE INDUCTOR

BACKGROUND OF THE INVENTION

The present invention relates to oximeters, and in particular to LED drive circuits in pulse oximeters.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed at various wavelengths is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

The light sources, typically light emitting diodes (LEDs), need to be driven with current to activate them. Because of the significant amount of current required, this can interfere with reducing power consumed by an oximeter. One solution is shown in U.S. Pat. No. 6,226,539. There, an inductor and capacitor circuit is used to first store charge in a first switch position, and then subsequently, in a second switch position, deliver that stored charge to the LED. Two different inductor and capacitor circuits are used, one for each LED. It would be desirable to reduce the number of components required in the circuit of this patent.

BRIEF SUMMARY OF THE INVENTION

The present invention provides a light emitter drive circuit for an oximeter which utilizes a single inductor for driving multiple light emitters. The inductor is connected through a switching circuit to multiple energy storage circuits, such as capacitors. These are alternately charged up, using the same inductor. Subsequently, the capacitors are alternately discharged to activate their corresponding light emitters through the same inductor.

In another aspect of the present invention, the magnetic susceptibility of the LED drive circuit is reduced by using magnetic flux canceling in the inductor. In one embodiment, a toroidal inductor is used with geometric symmetry in its magnetic flux. In another embodiment, a dual core closed bobbin shielded inductor is used. This embodiment has windings of both cores in series that are used to cancel the effect of an external magnetic field.

For a further understanding of the nature and advantages of the present invention, reference should be made to the following description taken in conjunction with the accompanying drawings.

DETAILED DESCRIPTION OF THE INVENTION

Oximeter System

Figure 1:
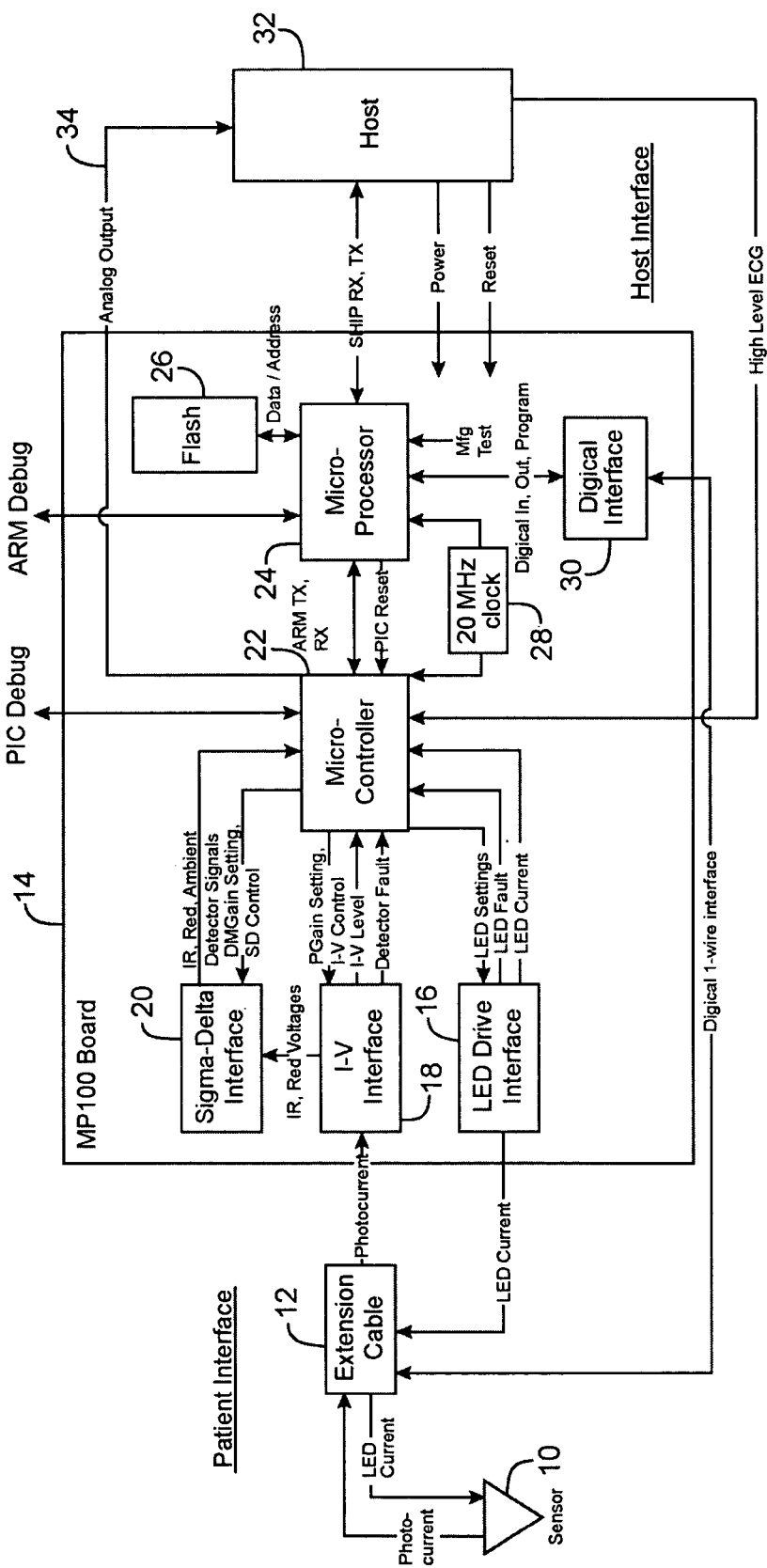
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22. Microcontroller 22 includes flash memory for a program, and SRAM memory for data. The processor also includes a microprocessor chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

LED Drive Circuit

Figure 2:
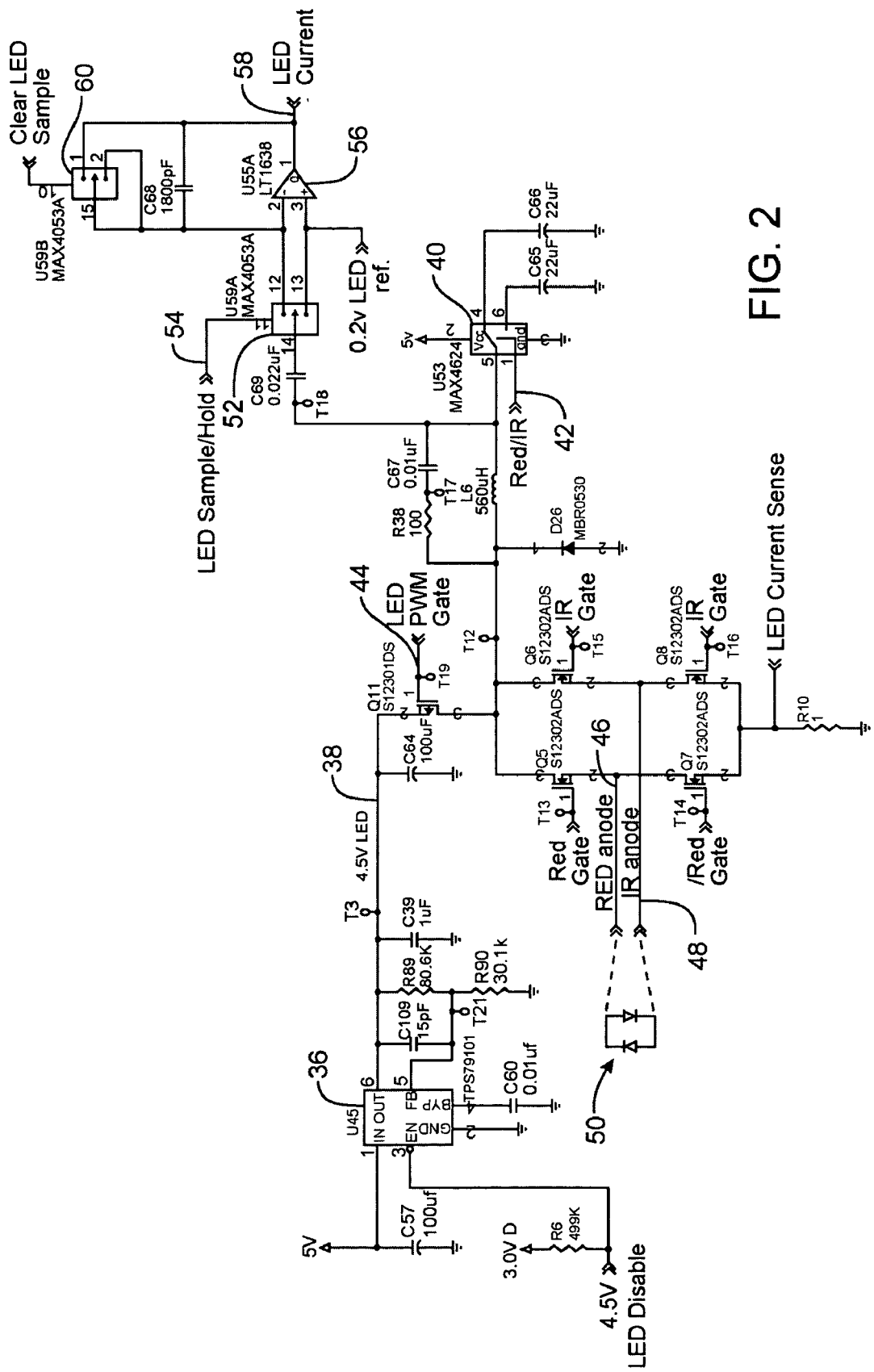
FIG. 2 is a circuit diagram of a LED drive circuit according to an embodiment of the present invention.

FIG. 2 is a circuit diagram of the LED drive circuit according to an embodiment of the invention, which forms a portion of LED drive interface 16 of FIG. 1. A voltage regulator 36 provides a voltage separate from the voltage supply for the overall oximeter circuitry. The output is provided as a 4.5 volt signal on line 38, with the level being set by the feedback resistor divider of resistors R89 and R90. The voltage on line 38 is provided to a FET transistor Q11 to an inductor L6. The current through inductor L6 is provided by a switch 40 to one of capacitors C65 and C66, which store charge for the red and IR LEDs, respectively. A red/IR control signal on line 42 selects the switch position under control of the oximeter processor. A control signal LED PWM gate on line 44 controls the switching of transistor switch Q11.

Once the capacitors are charged up, the control signal on line 44 turns off switch Q11 and current is provided from either capacitor C65 or C66, through switch 40 and inductor L6 to either the red anode line 46 or the IR anode line 48 by way of transistors Q5 and Q6, respectively. A signal "red gate" turns on transistor Q5, while its inverse, "/red gate" turns off transistor Q7. This provides current through the red anode line 46 to the back to back LEDs 50, with the current returning through the IR anode to transistor Q8 and through resistor R10 to ground. Transistor Q8 is turned on by the signal "/IR gate" while the inverse of this signal, "IR gate"

turns off transistor Q6. The signals are reversed when the IR anode is to be driven, with the "IR gate" and "red gate" signals, and their inverses, changing state, so that current is provided through transistor Q6 to IR anode 48 and returns through red anode 46 and through transistor Q7 to resistor R10 and ground. The "LED current sense" signal is read for calibration purposes not relevant to the present invention.

When the current from the capacitor C65 or C66 is provided through inductor L6 to the LEDs, and that current is switched off at the desired time, transistor Q11 is turned on so that the remaining current during the transition can be dumped into capacitor C64. This addresses the fact that the FET transistor switching is not instantaneous. Subsequently, C64 will dump its current through Q11 and inductor L6 into the capacitors when they are recharged.

Resistor R38 and capacitor C67 are connected in parallel to inductor L6 to protect against signal spikes, and provide a smooth transition. Connected to inductor L6 is a sampling circuit with a switch 52 controlled by an LED sample hold signal on line 54 to sample the signals and provide them through an amplifier 56 to a "LED current" signal on line 58 which is read by the processor. Operational amplifier 56 operates between 4.5 volts and ground. Thus, a voltage reference slightly above ground, of 0.2 volts, is provided as a voltage reference on pin 3. An integrating capacitor C68 is provided in parallel to amplifier 56. A switch 60 responds to a "clear LED sample" signal to operate the switch to short out the capacitor between samples.

The sample and hold circuit measures the voltage at node T18, between capacitor C69 and inductor L6, to determine the current. Capacitor C69 is 1/1000 of the value of capacitors C65 and C66. Thus, a proportional current is provided through C69, which is injected through switch 52 to integrating capacitor C68 to provide a voltage which can be measured at the output of amplifier 56 on line 58. The voltage measured by the processor on line 58 is used as a feedback, with the processor varying the width of the pulse delivered to transistor Q11 to selectively vary the amount of energy that's delivered to the capacitors 65 and 66, and then is eventually discharged to the LEDs 50. A PI (Proportional Integral) loop inside the processor then controls the PWM signal at Q11. This allows precise control of the LED intensity, allowing it to be maximized, if desired, without exceeding the desired limits (to avoid burning the patient, etc.).

The lower left of the diagram shows a "4.5 v LED disable" signal which is used by the microprocessor to turn off the voltage regulator 36 in certain instances. For example, diagnostics looking for shorts in a new sensor plugged in will turn off the voltage regulator if there is a problem with the LED line.

Figure 3:
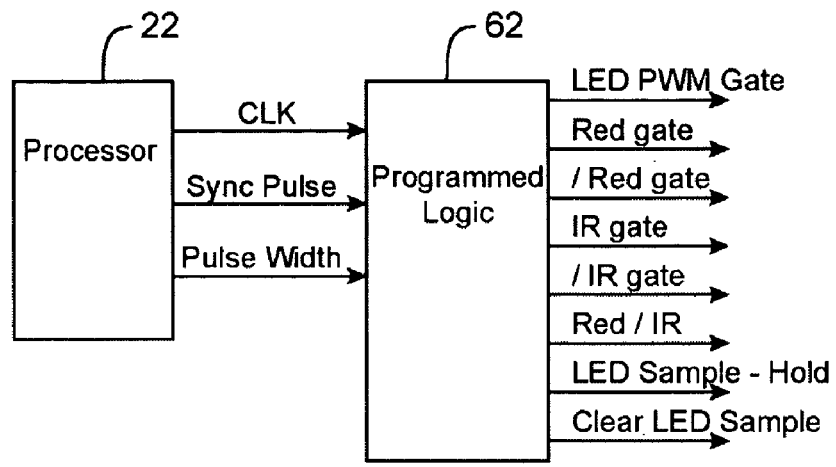
FIG. 3 is a block diagram of one embodiment of the logic for generating the timing and control signals for the circuit of FIG. 2.

FIG. 3 illustrates processor 22, from FIG. 1, connected to programmed logic 62, which is in the LED drive interface 16 in FIG. 1. Programmed logic 62 provides the different control signals used by the circuit of FIG. 2 in response to basic timing signals from the processor of a clock, a sync pulse, and a pulse width signal.

Thus, the present invention provides an improvement over the circuit shown in U.S. Pat. No. 6,226,539 by moving the switch position between the inductor and the capacitors to eliminate the need for two inductors. This not only reduces the part count, requiring only one inductor instead of two, but also provides better matching between the red and IR drive currents since both use the same inductor.

Figure 4:
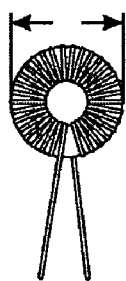
FIG. 4 is a diagram of a toroidal inductor used in one embodiment of the present invention.
Figure 5:
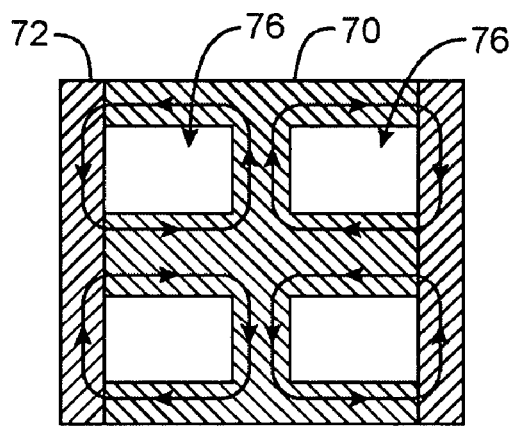
FIGS. 5 and 6 are diagrams of a dual core inductor according to an embodiment of the present invention.
Figure 6:
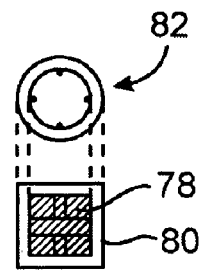

In another aspect of the invention, the LED drive circuit's susceptibility to magnetic interference is reduced. This magnetic interference can distort the detected pleth waveform. This is minimized by using magnetic flux canceling in the inductor. In one embodiment, this is a toroidal inductor as shown in FIG. 4. The toroidal inductor has a geometric symmetry in its magnetic flux. Another embodiment uses a dual core closed bobbin shielded inductor, such as shown in FIGS. 5 and 6. The windings of both cores in series are used to cancel the effect of an external magnetic field. These magnetic flux canceling inductors can be used either in the circuit of FIG. 2, or could be used in the dual inductor embodiment of the prior art. FIG. 5 shows the dual core inductor with a bobbin 70 in a cylinder 72. The wires are wound through gaps 76, as shown in FIG. 6. A first winding 78 is clockwise, while a second winding 80 is counterclockwise. A top view 82 is also shown. Ideally, the combined inductance in one embodiment is 680 uH.

The invention as illustrated in the embodiment of FIG. 2 enables the multiplexing of current, through an H-bridge topology, to back-to-back LEDs. Alternately, a different number of loads could be provided. The present invention is scalable to N-loads. The present invention provides significant efficiencies through reduction of support components, choice of components, and the properties of "loss-less" capacitor and inductor storage devices. The circuit of FIG. 2 can handle a range of forward voltage drops across the LEDs. The voltage provided varies automatically in accordance with the LED voltage drop, and does not put out more energy than it needs to.

The circuit is dynamically controlled through a PI loop in the processor, with current feedback being provided by the capacitive current divider from each storage capacitor (C65 and C66), which provides isolation. The feedback can be calibrated with a traditional in-line sense resistor, R10. In addition, this technique allows adjustment of the peak current for optimal signal-to-noise during the sampling period.

The addition of the upstream linear regulator 36 enhances power supply rejection capability, while the PI loop provides additional power supply insensitivity (to drift, P—P, surge, etc.).

As will be appreciated by those with skill in the art, the present invention can be embodied in other specific forms without departing from the essential characteristics thereof. For example, instead of two drive lines, three drive lines could be provided by adding another leg with FET transistor switches connected to the inductor. Additionally, this could be scalable to more than three legs connected in parallel, similar to the leg of Q6, Q8, and the leg of Q5, Q7. Accordingly, the foregoing description is intended to be illustrative, but not limiting, of the scope of the invention which is set forth in the following claims.

What is claimed is:

1. A light emitter drive circuit for an oximeter comprising:
   a voltage generating circuit;
   an inductor coupled to the voltage generating circuit;
   a first switching circuit coupled to a first node of the inductor;
   first and second energy storage circuits connected to the first switching circuit, such that current from the inductor can be steered by the first switching circuit to one of the energy storage circuits;
   a second switching circuit coupled to a second node of the inductor, wherein the second switching circuit has an H-bridge drive circuit including four transistors; and
   first and second light emitter drive lines connected to the second switching circuit, such that energy from the first and second energy storage circuits can be alternately coupled to the first and second light emitter drive lines, and wherein the drive lines are configured to drive light emitters that are back-to-back.

2. An LED circuit for an oximeter comprising:
a voltage generating circuit;
an inductor coupled to the voltage generating circuit;
a first switching circuit coupled to a first node of the inductor;
first and second capacitors connected to the first switching circuit, such that current from the inductor can be steered by the first switching circuit to one of the capacitors;
an H-bridge drive switching circuit including four transistors coupled to a second node of the inductor; and
first and second light emitter drive lines, for LEDs in a back-to-back configuration, in the middle of the H-bridge, such that energy from the first and second capacitors can be alternately coupled to the first and second light emitter drive lines.

3. The circuit of claim 2 wherein the inductor is a toroidal inductor.

4. The circuit of claim 2 wherein the inductor is a dual core closed bobbin shielded inductor.

* * * * *